US010478262B2

(12) United States Patent
Niese et al.

(10) Patent No.: US 10,478,262 B2
(45) Date of Patent: Nov. 19, 2019

(54) ORTHOPAEDIC INSTRUMENT SYSTEM INCLUDING AN INSTRUMENT CADDY AND METHOD FOR ASSEMBLING A SURGICAL INSTRUMENT

(71) Applicant: DEPUY IRELAND UNLIMITED COMPANY, Co Cork (IE)

(72) Inventors: Justin M. Niese, Fort Wayne, IN (US); Rebecca L. Chaney, Warsaw, IN (US); Stephanie M. Wainscott, Warsaw, IN (US); Oliver Coultrup, Leeds (GB); Alasdair Mercer, Leeds (GB)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 0 days.

(21) Appl. No.: 15/830,457

(22) Filed: Dec. 4, 2017

(65) Prior Publication Data
US 2019/0167375 A1   Jun. 6, 2019

(51) Int. Cl.
| | |
|---|---|
| *A61B 50/33* | (2016.01) |
| *A61B 17/16* | (2006.01) |
| *B65D 25/10* | (2006.01) |
| *B65D 1/34* | (2006.01) |
| *A61B 50/30* | (2016.01) |
| *A61B 17/00* | (2006.01) |

(52) U.S. Cl.
CPC .......... *A61B 50/33* (2016.02); *A61B 17/1659* (2013.01); *A61B 17/1675* (2013.01); *B65D 1/34* (2013.01); *B65D 25/107* (2013.01); *A61B 2017/00526* (2013.01); *A61B 2050/3008* (2016.02)

(58) Field of Classification Search
CPC . A61B 17/16; A61B 17/1659; A61B 17/1675; A61B 50/33; A61B 2050/3008; A61B 2017/00526; B65D 1/34; B65D 1/36; B65D 25/10; B65D 25/107; B65D 83/10
USPC ......................................... 206/363–370, 438
See application file for complete search history.

(56) References Cited

U.S. PATENT DOCUMENTS

| | | | | |
|---|---|---|---|---|
| 3,697,223 A | * | 10/1972 | Kovalcik et al. ......... | A61L 2/26 206/370 |
| 5,174,453 A | | 12/1992 | Stoeffler | |
| 5,339,955 A | * | 8/1994 | Horan .................... | A61B 50/33 206/370 |
| 5,381,896 A | * | 1/1995 | Simons .................. | B65D 25/10 206/370 |

(Continued)

FOREIGN PATENT DOCUMENTS

| | | |
|---|---|---|
| EP | 2668932 A1 | 12/2013 |
| WO | 2017034845 A1 | 3/2017 |

OTHER PUBLICATIONS

Extended European Search Report for Application No. 18207380.9, dated Jul. 3, 2019, 8 pages.

*Primary Examiner* — Bryon P Gehman
(74) *Attorney, Agent, or Firm* — Barnes & Thornburg LLP

(57) ABSTRACT

An orthopaedic instrument system including an instrument caddy is disclosed. The instrument caddy is configured to receive one or more cutting broaches to house the cutting broaches between orthopaedic surgical procedures. The instrument caddy is also configured to be used during a surgical procedure to assist a user in assembling the cutting broach with another surgical instrument. A method of assembling a surgical instrument is also disclosed.

19 Claims, 18 Drawing Sheets

(56) References Cited

U.S. PATENT DOCUMENTS

| | | | |
|---|---|---|---|
| 5,451,380 A * | 9/1995 | Zinnanti | A61L 2/26 |
| | | | 206/370 |
| 5,732,821 A | 3/1998 | Stone et al. | |
| 5,848,693 A * | 12/1998 | Davis | A61B 50/33 |
| | | | 206/370 |
| 5,984,097 A * | 11/1999 | Kalinski | A61B 17/06114 |
| | | | 206/366 |
| 6,331,280 B1 * | 12/2001 | Wood | A61L 2/26 |
| | | | 206/370 |
| 6,368,565 B1 | 4/2002 | Michaelson et al. | |
| 7,066,328 B2 * | 6/2006 | Pulsifer | A61B 50/22 |
| | | | 206/363 |
| 9,084,593 B2 * | 7/2015 | Yakel | A61B 50/362 |
| 9,113,918 B2 * | 8/2015 | Chaney | A61B 17/164 |
| 2005/0241965 A1 | 11/2005 | Kurc | |

\* cited by examiner

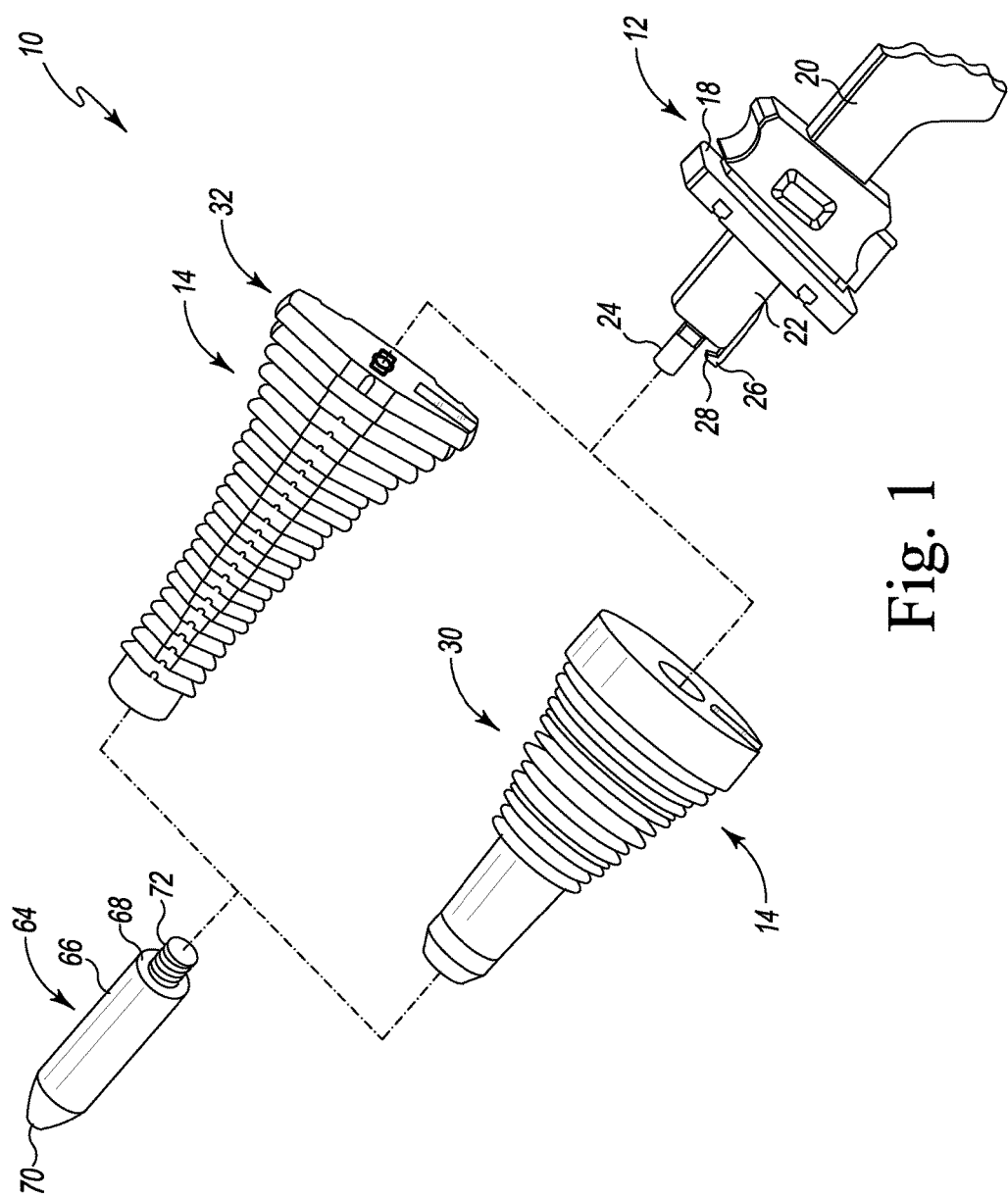

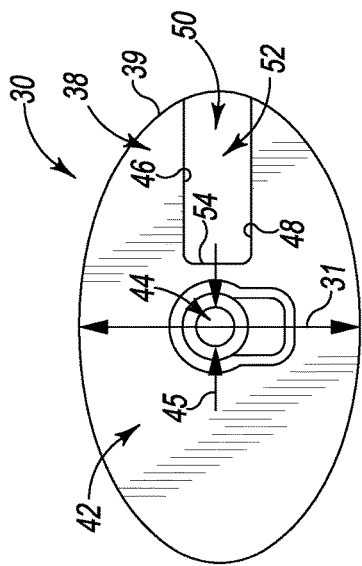
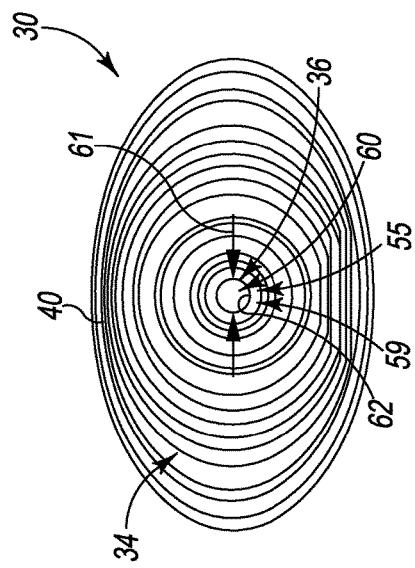
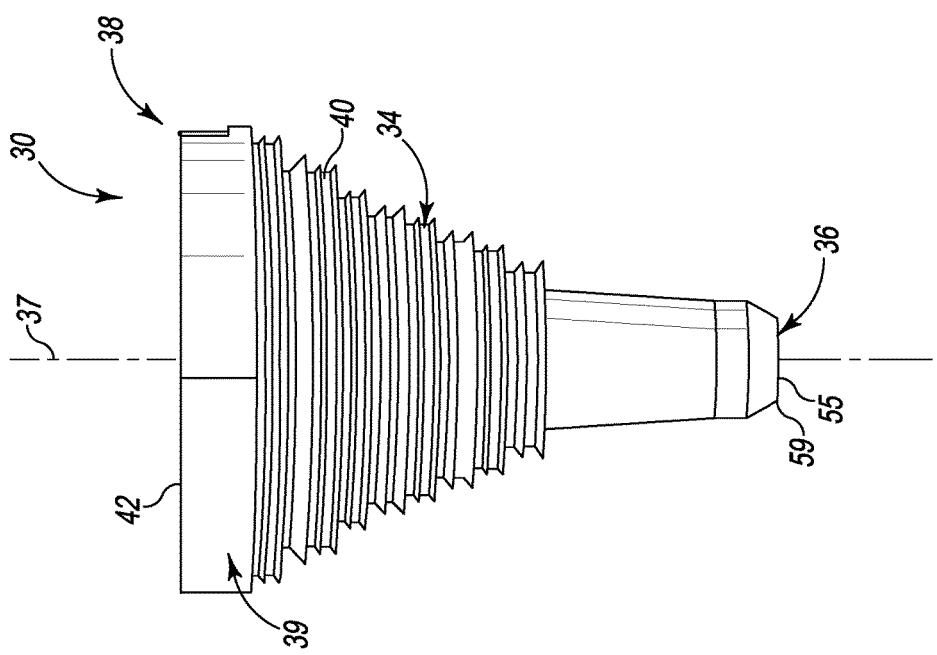

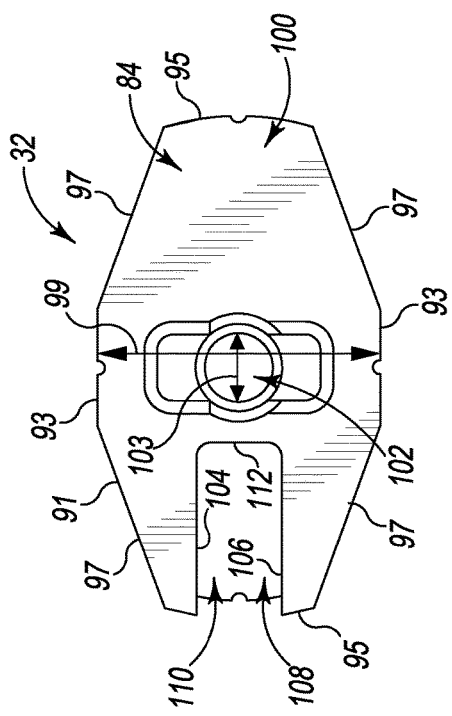
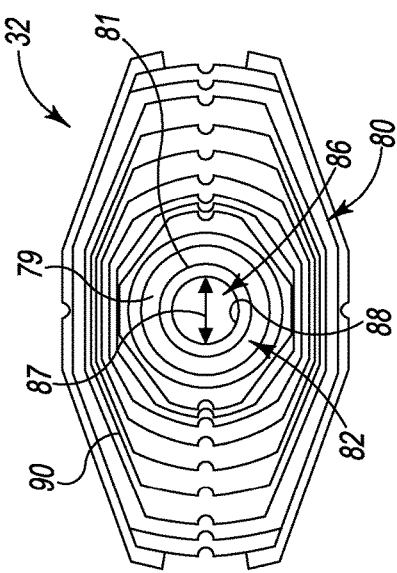
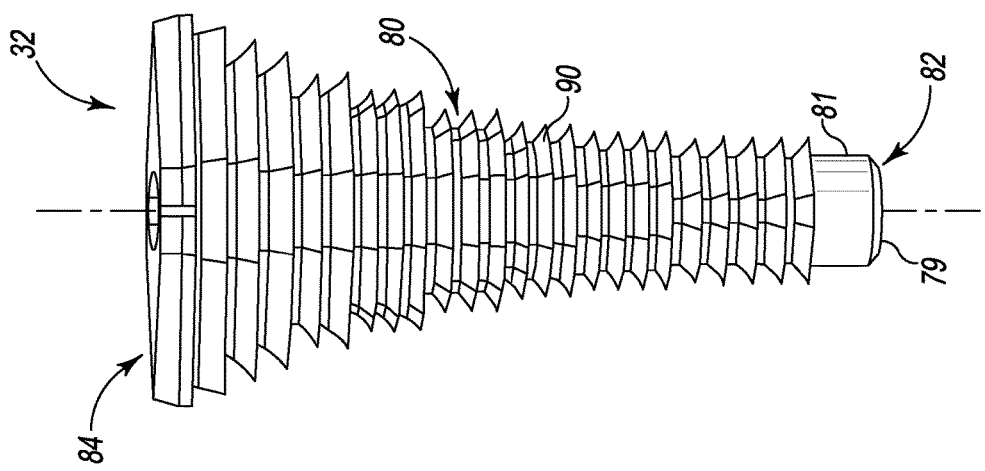

US 10,478,262 B2

ORTHOPAEDIC INSTRUMENT SYSTEM INCLUDING AN INSTRUMENT CADDY AND METHOD FOR ASSEMBLING A SURGICAL INSTRUMENT

TECHNICAL FIELD

The present disclosure relates generally to orthopaedic instruments for use in the performance of an orthopaedic joint replacement procedure, and, more particularly, to an instrument caddy for an orthopaedic surgical instrument tray used in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes multiple prosthetic components, including a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During any knee surgery, the orthopaedic surgeon typically uses a variety of different orthopaedic surgical instruments such as, for example, broaches, cutting blocks, reamers, drill guides, and other surgical instruments to prepare the patient's bones to receive the knee prosthesis. The instruments are generally organized within an instrument tray that is accessible to the surgeon throughout the procedure. During the procedure, the surgeon or other user removes various instruments from the tray for use in the procedure.

SUMMARY

According to one aspect of the disclosed embodiments, an orthopaedic instrument system includes a cutting broach including a tapered body extending along a longitudinal axis from a base to a tip. A plurality of cutting teeth are defined in the tapered body. An instrument caddy is configured to receive the cutting broach. The caddy includes a bottom wall, a first side wall extending upwardly from the bottom wall, and a second side wall spaced apart from the first side wall and extending upwardly from the bottom wall to define a storage chamber. The first side wall includes an opening and a pair of surfaces extending inwardly from the opening to define a groove sized to receive the base of the cutting broach. The pair of surfaces are shaped to engage the base of the cutting broach to inhibit rotation of the cutting broach about its longitudinal axis. A slot aligned with the groove extends through the second side wall. The slot is sized to receive the tip of the cutting broach.

In some embodiments, a stem component may have an elongated body and a mounting end sized to be received in an opening defined in an end surface of the tip of the cutting broach to couple the stem component to the cutting broach. When the cutting broach is positioned in the caddy, the end surface of the tip of the cutting broach may extend outwardly from the slot to permit the stem component to be coupled to the cutting broach. In some embodiments, when the cutting broach is positioned in the caddy, the mounting end of the stem component may be received within the slot to permit the stem component to be coupled to the cutting broach.

In some embodiments, the cutting broach may be a first cutting broach, the opening may be a first opening, and the slot may be a first slot. The caddy may include a second opening in the second sidewall and a second pair of surfaces extending inwardly from the second opening to define a second groove sized to receive a base of a second cutting broach. A second slot extending through the first sidewall may be sized to receive a tip of the second cutting broach.

In some embodiments, the system may have a plurality of cutting broaches. The first side wall may have a plurality of grooves. Each groove may be sized to selectively receive a base of one of the plurality of cutting broaches. The caddy may have a plurality of slots extending through the second side wall. Each slot may be aligned with one of the plurality of grooves and sized to receive a tip of one of the plurality of cutting broaches.

In some embodiments, an instrument tray may be sized and shaped to receive the caddy.

In some embodiments, the caddy may have an end wall extending between the first side wall and the second side wall. A handle may be formed in the end wall. The handle may be an opening extending through the end wall. The handle may be a flange extending from the end wall.

In some embodiments, the cutting broach may be one of a femoral cutting broach and a tibial cutting broach.

According to another aspect of the disclosed embodiments, an orthopaedic instrument system includes an instrument caddy configured to receive a cutting broach. The caddy includes a bottom wall, a first side wall extending upwardly from the bottom wall, and a second side wall spaced apart from the first side wall and extending upwardly from the bottom wall to define a storage chamber. The first side wall includes an opening and a pair of surfaces extending inwardly from the opening to define a groove sized to receive a base of the cutting broach. A slot aligned with the groove extends through the second side wall. The slot is sized to receive a tip of the cutting broach.

In some embodiments, the system may have a cutting broach having a tapered body extending along a longitudinal axis from a base to a tip. A plurality of cutting teeth may be defined in the tapered body. An opening may be defined in an end surface of the tip.

In some embodiments, the slot may be defined by a pair of side walls that are spaced apart a distance greater than the diameter of the opening defined in the end surface of the tip of the cutting broach.

In some embodiments, the system may have a stem component having an elongated body and a mounting end sized to be received in the opening defined in the end surface of the tip of the cutting broach to couple the stem component to the cutting broach.

In some embodiments, the first side wall may have a plurality of grooves. Each groove may be sized to receive a base of one of a plurality of cutting broaches. A plurality of slots may extend through the second side wall. Each slot may be aligned with a groove of the plurality of grooves and be sized to receive a tip of one of the plurality of cutting broaches.

In some embodiments, the caddy may have an end wall extending between the first side wall and the second side wall. A handle may be formed in the end wall. The handle may be an opening extending through the end wall. The handle may be a flange extending from the end wall.

In some embodiments, the cutting broach may be at least one of a femoral cutting broach or a tibial cutting broach.

According to yet another aspect of the disclosed embodiments, a method of assembling a surgical instrument includes selecting a cutting broach positioned in an instrument caddy. The cutting broach includes a tapered body extending along a longitudinal axis from a base to a tip and a plurality of cutting teeth defined in the tapered body. The method also includes advancing a mounting end of a stem component through a slot extending through a side wall of the instrument caddy. The method also includes coupling the mounting end of the stem component to the tip of the cutting broach positioned within the slot of the instrument caddy. The method also includes gripping the stem component to remove the cutting broach from the instrument caddy.

In some embodiments, coupling the mounting end of the stem component to a tip of the cutting broach positioned within the slot of the surgical instrument caddy may require threading the mounting end of the stem component into the tip of the cutting broach. A pair of surfaces of the surgical instrument caddy may engage the base of the cutting broach to inhibit rotation of the cutting broach about the longitudinal axis of the base during the threading of the mounting end of the stem component into the tip of the cutting broach.

BRIEF DESCRIPTION

The detailed description particularly refers to the following figures, in which:

FIG. 1 is an exploded view of an orthopaedic surgical instrument system;

FIG. 2 is a side elevation view of a tibial broach of the orthopaedic instrument system of FIG. 1;

FIG. 3 is a top plan view of the tibial broach shown in FIG. 2;

FIG. 4 is a bottom plan view of the tibial broach shown in FIG. 2;

FIG. 5 is a side elevation view of a femoral broach of the orthopaedic instrument system of FIG. 1;

FIG. 6 is a top plan view of the femoral broach shown in FIG. 5;

FIG. 7 is a bottom plan view of the femoral broach shown in FIG. 5;

DETAILED DESCRIPTION

Figure 8:
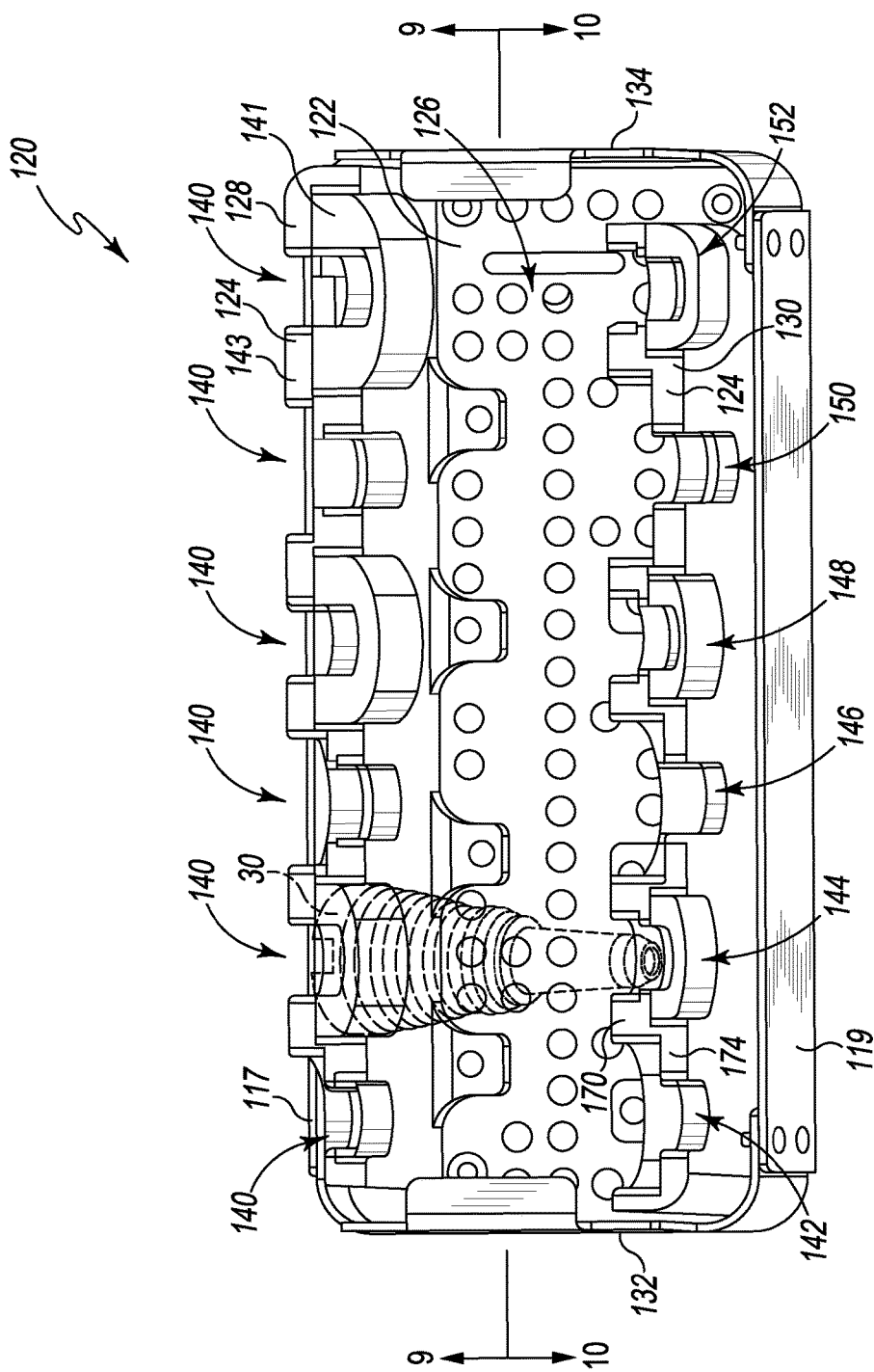
FIG. 8 is a perspective view of a surgical instrument caddy.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an orthopaedic surgical instrument system 10 includes an instrument 12 that attaches to one of a plurality of cutting broaches 14. As described in greater detail below, the orthopaedic surgical instrument system 10 includes surgical instrument caddies 120, 300 that house the cutting broaches 14 between orthopaedic surgical procedures. Each of the instrument caddies 120, 300 is also configured to be used during a surgical procedure to assist a user in assembling each cutting broach 14 with another surgical instrument such as, for example, a stem component 64 or the instrument 12.

The plurality of cutting broaches 14 include a tibial cutting broach 30 (shown in detail in FIGS. 2-4) and a femoral cutting broach 32 (shown in detail in FIGS. 5-7). Referring now to FIGS. 2-4, the tibial broach 30 includes an outer surface 34 extending from a tip 36 to a base 38 along a longitudinal axis 37. The outer surface 34 is tapered, with the diameter of the broach 30 decreasing from the base 38 to the tip 36. A plurality of cutting teeth 40 are formed in the outer surface 34 and are configured to remove portions of the patient's tibia when the tibial broach 30 is inserted into a medullary canal formed in the patient's tibia. The cutting teeth 40 are configured to engage the bone surrounding the medullary canal when the broach 30 is inserted in the medullary canal. The cutting teeth 40 cover the outer surface 34 such that the tibial broach 30 cannot be easily picked up by a surgeon or other user without risk of the surgeon or other user cutting his/her hand. It should be appreciated that other broaches having different configurations may be provided. For example, the outer diameter and/or length of the broach may vary to produce different sized canals to accommodate prosthetic components of different sizes.

The base 38 of the tibial broach 30 includes an oval-shaped outer surface 39 and a substantially planar top surface 42 defined within the oval-shaped outer surface 39. The minor axis of the oval-shaped outer surface 39 defines a width 31 of the tibial broach 30. A bore 44 having a diameter 45 is defined in the top surface 42. Inner walls 46, 48 extend downwardly from the top surface 42 and cooperate with a bottom wall 50 to define a slot 52 in the tibial broach 30. The slot 52 extends through the outer surface 34 of the tibial broach 30. A flange 54 extends between the inner walls 46, 48.

The tip 36 of the tibial broach 30 includes a circular outer surface 59 and an end surface 55 defined within the outer surface 59. An opening 60 is defined in the end surface 55 and has a diameter 61 that is less than a diameter 57 of the outer surface 59. A threaded inner wall 62 of the opening 60 is shaped to receive the stem component 64 (shown in FIG. 1). Referring to FIG. 1, the stem component 64 includes an elongated body 66 that extends from an end 68 to a tip 70. A plurality of threads 72 are defined on the end 68 to engage the threaded inner wall 62 of the tibial broach 30. In some embodiments, the stem component 64 may be coupled to the tibial broach 30 by other means, e.g. snap-fit fastener, bolted fastener, or bayonet fastener. In an exemplary embodiment, a plurality of stem components 64 may be provided having different lengths and diameters. For example, the diameter of the stem component 64 may vary between 10 millimeters and 24 millimeters.

Referring to FIGS. 5-7, the femoral broach 32 includes an outer surface 80 extending from a tip 82 to a base 84 along a longitudinal axis 83. The tip 82 of the femoral broach 32 includes a circular outer surface 81 and an end surface 79 defined within the outer surface 81. An opening 86 is defined in the end surface 79 and has a diameter 87 that is less than a diameter 89 of the outer surface 81. The opening 86 has a threaded inner wall 88 that engages the threads 72 of the stem component 64. In some embodiments, the stem component 64 may be coupled to the femoral broach 32 by other means, e.g. snap-fit fastener, bolted fastener, or bayonet fastener. The outer surface 80 is tapered, with the diameter of the broach 32 decreasing from the base 84 to the tip 82. A plurality of cutting teeth 90 are formed in the outer surface 80 and are configured to remove portions of the patient's femur when the femoral broach 32 is inserted into a medullary canal formed in the patient's femur. The cutting teeth 90 are configured to engage the bone surrounding the medullary canal when the broach 32 is inserted in the medullary canal. The cutting teeth 90 cover the outer surface 80 such that the femoral broach 32 cannot be easily picked up by a surgeon or other user without risk of the surgeon or other user cutting his/her hand. It should be appreciated that other broaches having different configurations may be provided. For example, the outer diameter and/or length of the broach may vary to produce different sized canals to accommodate prosthetic components of different sizes.

The base 84 of the femoral broach 32 includes an outer surface 91 including a pair of end surfaces 93 and a pair of side surfaces 95. Angled surfaces 97 extend between the end surfaces 93 and the side surfaces 95. A width 99 of the base 84 is defined between the side surfaces 95. A substantially planar top surface 100 is defined at the base 84 within the outer surface 91. A bore 102 having a diameter 103 is defined in the top surface 100. Inner walls 104, 106 extend downwardly from the top surface 100 and cooperate with a bottom wall 108 to define a slot 110 that extends through the outer surface 80. A flange 112 extends between the inner walls 104, 106.

Referring back to FIG. 1, the instrument 12 has a base 18 and a handle 20 extending from the base 18. A plug 22 is secured to the base 18 opposite the handle 20. A post 24 extends from the plug 22 and is configured to be received in the bore 44 of tibial broach 30 or the bore 102 of femoral broach 32 when the instrument 12 is secured to broach 14. The instrument 12 includes a lever 26 configured to retain the instrument 12 on the broach 14. In the illustrative embodiment, the lever 26 includes a flange 28 configured to engage the broach 14 when the post 24 is received in the broach 14. The flange 28 engages one of the flange 54 of the tibial broach 30 or the flange 112 of the femoral broach 32. It should be appreciated that in other embodiments the instrument 12 may include latches, pins, or other fasteners to secure the instrument 12 to the broach 14.

Referring now to FIG. 8, one of the surgical instrument caddies of the system 10 (i.e., the caddy 120) is shown. In the illustrative embodiment, the caddy 120 is configured to receive a plurality of tibial broaches 30 of different sizes, including the tibial broach 30 described above. As shown in FIG. 8, the caddy 120 is configured to house up to six tibial broaches, with sizes that range from 29 millimeters to 69 millimeters. It should be appreciated that other size ranges are possible in other embodiments and the caddy may be configured to receive additional or fewer broaches.

Figure 9:
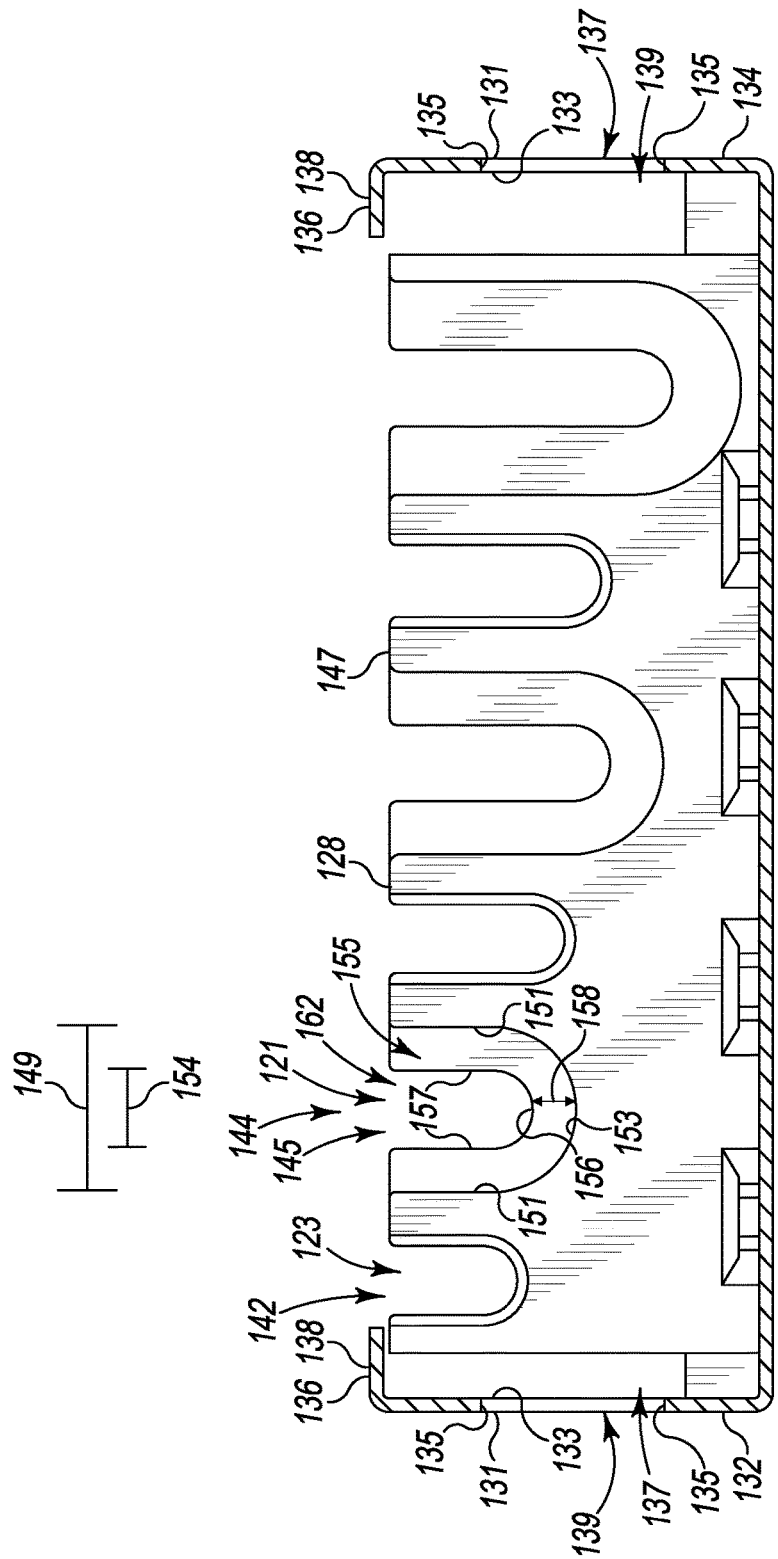
FIG. 9 is a cross-sectional elevation view of the surgical instrument caddy taken along the line 9-9 in FIG. 8.
Figure 10:
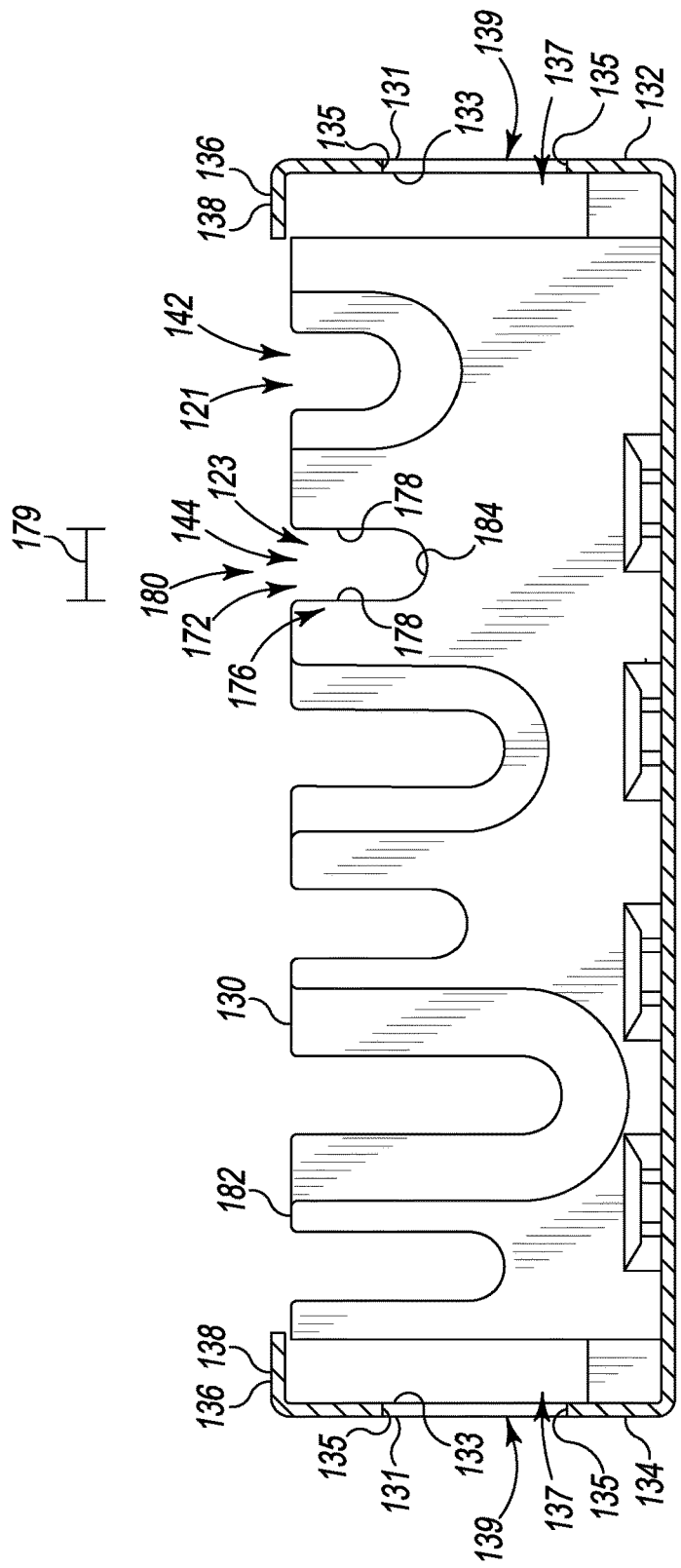
FIG. 10 is a cross-sectional elevation view of the surgical instrument caddy taken along the line 10-10 in FIG. 8.

The caddy 120 includes a bottom wall 122, a pair of outer walls 117, 119, and a pair of end walls 132, 134 positioned at the ends of the outer walls 117, 119. The bottom wall 122, outer walls 117, 119, and end walls 132, 134 are preferably formed from metal. As shown in FIGS. 9-10. Each of the end walls 132, 134 includes an inner opening 131 and an outer opening 133. Side surfaces 135 extend between the inner opening 131 and the outer opening 133 to define a bore 137 through each of the end walls 132, 134. The bore 137 forms a handle 139 which may be used to lift the caddy 120. Also, a flange 136 extends inwardly from each end wall 132, 134. The flange 136 also forms a handle 138 that may be used to lift the caddy 120.

Referring back to FIG. 8, a plurality of side walls 124 extends upwardly from the bottom wall 122 to define a storage chamber 126. The side walls 124 are positioned between the outer walls 117, 119 and the end walls 132, 134. The side walls 124 are preferably formed from plastic. The side walls 124 include a pair of longitudinal walls 128, 130. As described in greater detail below, the longitudinal walls 128, 130 cooperate to define six broach carriers 140 that are configured to receive the six tibial broaches 30. A broach carrier 142 is positioned adjacent the end wall 132. A second broach carrier 144 is positioned next to the broach carrier 142. Additional broach carriers 146, 148, 150, and 152 are positioned between the broach carrier 144 and the end wall 134 with the broach carrier 152 positioned adjacent the end wall 134. Each broach carrier 140 is configured to hold one of the tibial broaches 30 during sterilization or storage between surgical procedures, as well as assist the surgeon or other user to assemble a broach with a stem component and the instrument handle. In an exemplary embodiment, the broach carrier 142 is configured to retain a 29 millimeter tibial broach 30, the broach carrier 144 is configured to retain a 37 millimeter tibial broach 30, the broach carrier 146 is configured to retain a 45 millimeter tibial broach, the broach carrier 148 is configured to retain a 53 millimeter tibial broach, the broach carrier 150 is configured to retain a 60 millimeter tibial broach, and the broach carrier 152 is configured to retain a 69 millimeter tibial broach. The broach carriers 144, 146, 148, 150, and 152 are capable of retaining a smaller sized broach.

As shown in FIGS. 9-10, each broach carrier 140 includes a base receptacle 121 configured to receive the base 38 of a tibial broach 30 and a tip mount 123 configured to receive the tip 36 of the tibial broach 30. In the illustrative embodiment, the orientations of the broach carriers 140 alternate so that the broach carrier 144 has a base receptacle 121 defined in the longitudinal wall 128 and a corresponding tip mount 123 defined in the opposite longitudinal wall 130, while the broach carrier 142 has a base receptacle 121 defined in the longitudinal wall 130 and a corresponding tip mount 123 defined in the longitudinal wall 128. In the illustrative embodiment, the configuration of each carrier 140 (and hence each receptacle 121 and tip mount 123) is substantially identical so that only a single carrier 140 will be described in detail below.

Referring to FIG. 9, the base receptacle 121 of the broach carrier 144 includes a groove 155 that is defined in an inner surface 141 (shown in FIG. 8) of the longitudinal wall 128. The groove 155 is sized to receive the base 38 of a tibial broach 30. The base receptacle 121 also includes a channel 162 that is defined in an outer surface 143 (shown in FIG. 8) of the longitudinal wall 128. In the illustrative embodiment, the channel 162 opens into the groove 155. The groove 155 is partially defined by a pair of side surfaces 151 that extend inwardly from an opening 145 formed in a top surface 147 of the longitudinal wall 128. A rounded bottom surface 153 extends between the side surfaces 151 such that the side surfaces 151 and the bottom surface 153 cooperate to define the groove 155. The side surfaces 151 are spaced a distance 149 that corresponds to the width 31 of the base 38 of the tibial broach 30, and the bottom surface 153 is shaped to correspond to the oval-shaped outer surface 39 of the base 38 of the tibial broach 30 so that the groove 155 prevents rotation of the tibial broach 30 about its longitudinal axis 37.

The channel 162 is partially defined by a pair of side surfaces 157 extending inwardly from the opening 145. The side surfaces 157 are spaced a distance 154 that is less than the distance 149. The distance 154 is greater than the diameter 45 of the bore 44 of the tibial broach 30 so that the bore 44 is accessible through the channel 162. A rounded bottom surface 156 extends between the side surfaces 157. The bottom surface 156 is spaced a distance 158 from the bottom surface 153. The bottom surface 156 and the side surfaces 157 cooperate to define the channel 162.

Referring to FIG. 10, the tip mount 123 of the broach carrier 144 includes a slot 176 defined in an inner surface 170 (shown in FIG. 8) of the longitudinal wall 130. The slot 176 is sized to receive the tip 36 of a tibial broach 30. The tip mount 123 also includes a channel 172 that is defined in an outer surface 174 (shown in FIG. 8) of the longitudinal wall 130. In the illustrative embodiment, the channel 172 opens into the slot 176. The slot 176 is partially defined by pair of side surfaces 178 that extend inwardly from an opening 180 formed in a top surface 182 of the longitudinal wall 130. The side surfaces 178 are spaced a distance 179. A rounded bottom surface 184 extends between the side surfaces 178 such that the side surfaces 178 and the bottom surface 184 cooperate to define the slot 176. The bottom surface 184 is rounded to correspond to the rounded outer surface 59 of the tip 36 of the tibial broach 30.

Figure 11:
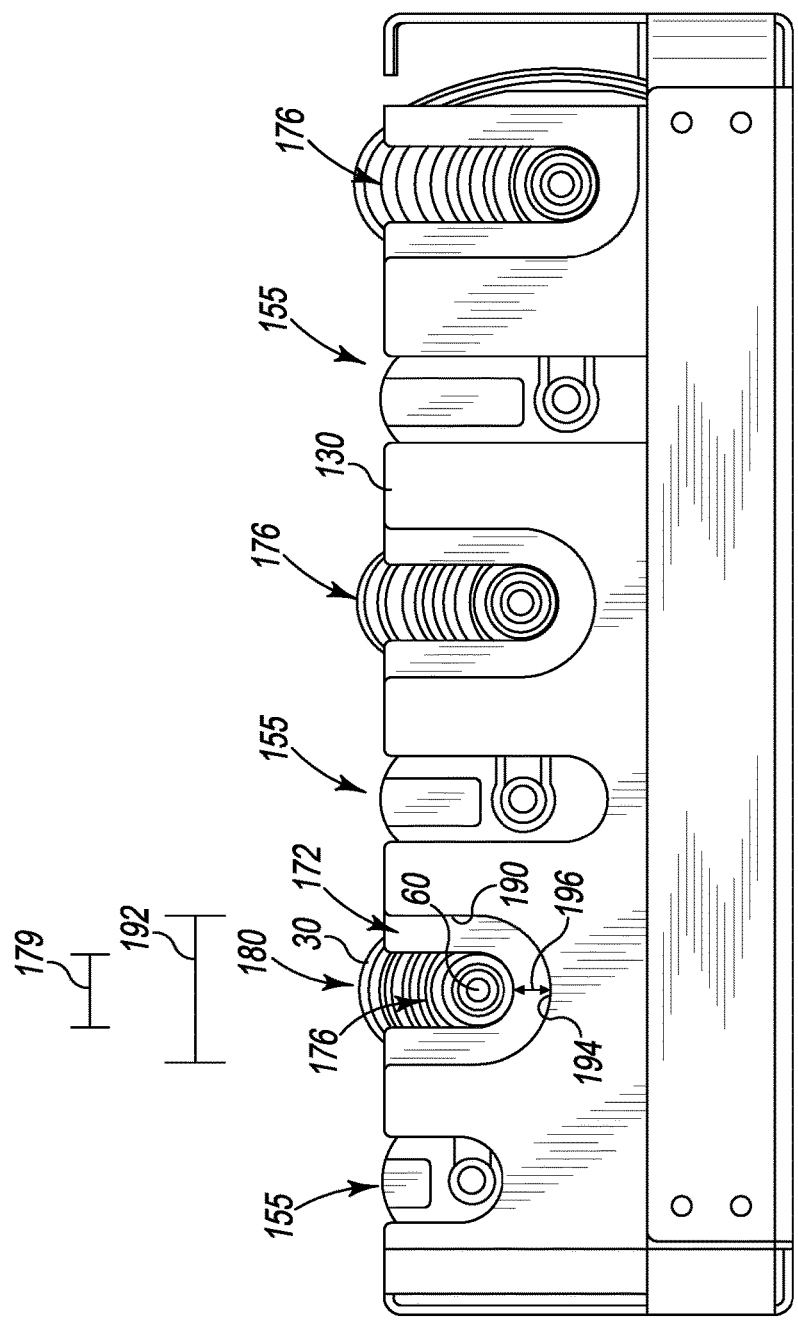
FIG. 11 is a front elevation view of the surgical instrument caddy shown in FIG. 8 with a number of tibial broaches positioned in the surgical instrument caddy.

Referring to FIG. 11, the channel 172 is partially defined by a pair of side surfaces 190 extending inwardly from the opening 180. The side surfaces 190 are spaced a distance 192 that is less than the distance 179. The distance 192 is greater than the diameter 61 of the opening 60 of the tibial broach 30 so that the opening 60 of the tibial broach 30 is accessible through the channel 172. A rounded bottom surface 194 extends between the side surfaces 190. The bottom surface 194 is spaced a distance 196 from the bottom surface 184.

Referring back to FIG. 8, although the configuration of the carriers 140 is substantially the same, the base receptacles 121 and tip mounts 123 increase in size from the end wall 132 to the end wall 134 to accommodate broaches of increasing size. Specifically, the base receptacles 121 and tip mounts 123 of the broach carrier 152 adjacent end wall 134 are deeper than the base receptacle 121 and tip mount 123 of the broach carrier 142 adjacent end wall 132. The groove 155, slot 176, and channels 162 and 172 of the broach carrier 152 are deeper than the groove 155, slot 176, and channels 162 and 172 of the broach carrier 142. Each of the intermittent broach carriers 144, 146, 148, 150 has a depth that is between the depth of the broach carrier 142 and the broach carrier 152.

Referring to FIG. 11, the grooves 155 and slots 176 alternate along the longitudinal wall 130. The bases 38 of respective tibial broaches 30 are positioned within respective grooves 155 and accessible through the channels 162. The distance 154 between the side surfaces 157 of the channel 162 is greater than the diameter 45 of the bore 44 of the tibial broach 30. Accordingly, the bore 44 is accessible through the channel 162 such that the instrument 12 can be attached to the tibial broach 30 while the tibial broach 30 is positioned within the caddy 120. Additionally, a size of the tibial broach 30 that may be printed on the tibial broach 30 is viewable through the channel 162. The tips 36 of respective tibial broaches 30 are positioned within respective slots 176 and accessible through the channels 172. The distance 192 between the side surfaces 190 of the channel 172 is greater than the diameter 61 of the opening 60 in the tip 36 of the tibial broach 30. In that way, the opening 60 is accessible through the channel 172 such that the stem component 64 can be attached to the tibial broach 30 while the tibial broach 30 is positioned within the caddy 120.

Figure 15:
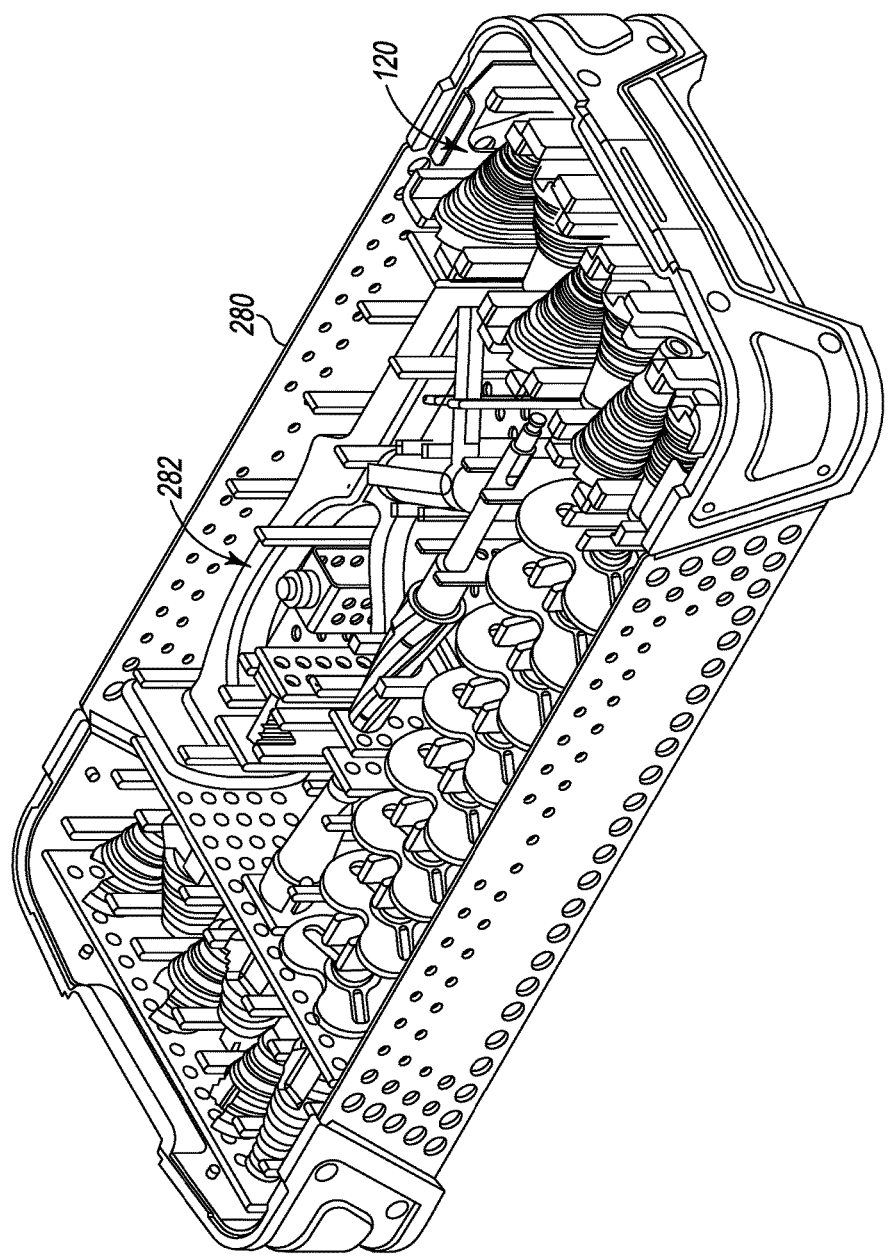
FIG. 15 is a perspective view of the surgical instrument caddy positioned within an orthopaedic instrument tray.

In use, the caddy 120 is positioned within an orthopaedic instrument tray 280, as illustrated in FIG. 15. The orthopaedic instrument tray 280 includes a plurality of instruments 282 that are utilized with the tibial broach 30 during joint arthroplasty. The caddy 120 rests within the orthopaedic instrument tray 280 to provide the surgeon or other user with access to the tibial broach 30 during the procedure. The caddy 120 may be removed from the orthopaedic instrument tray 280 utilizing one of the handles 138, 139 and placed on a surgical table. By removing the caddy 120 from the orthopaedic instrument tray 280, the tibial broach 30 may be removed from the caddy 120 with the stem component 64, as described below.

Figure 12:
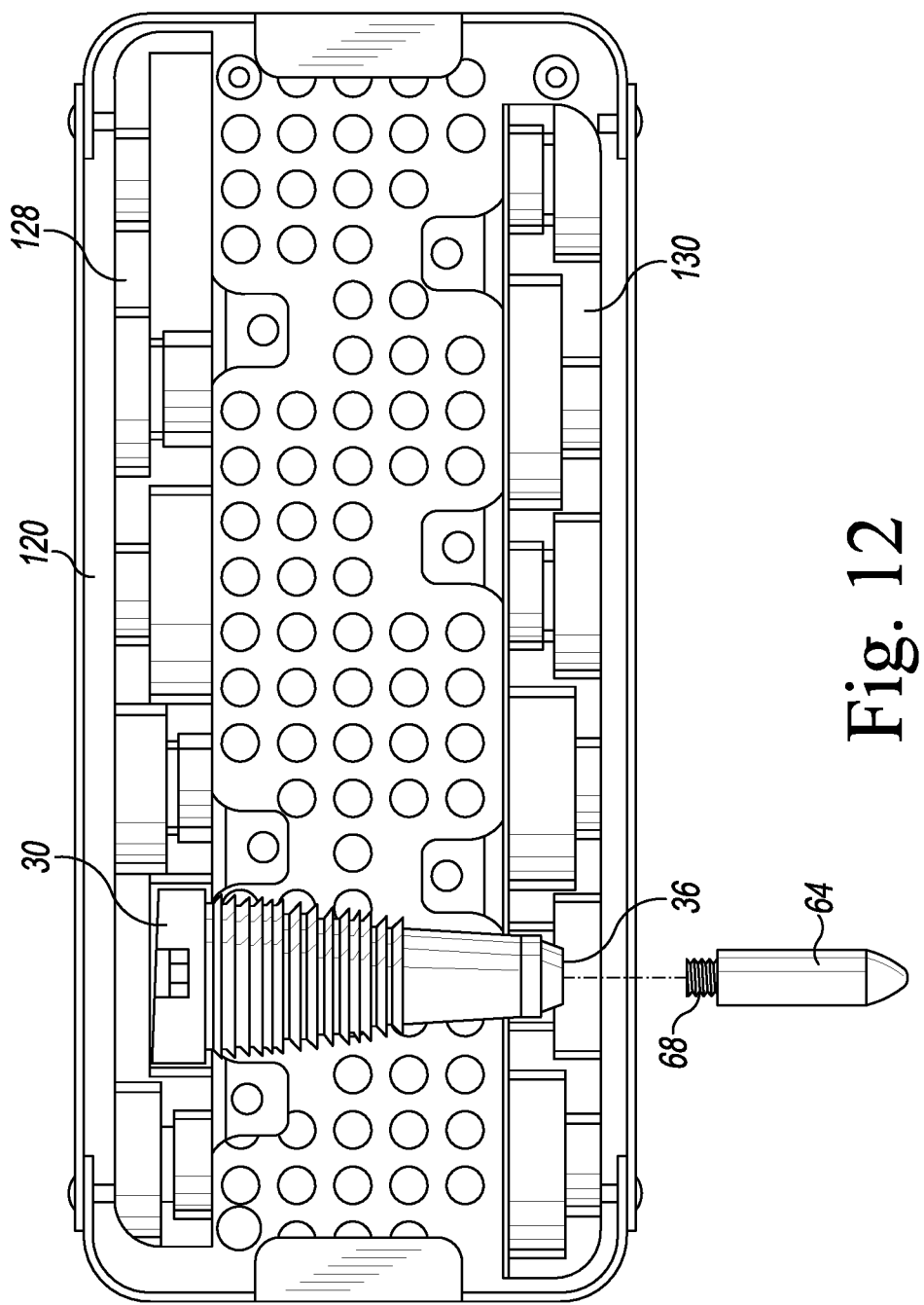
FIG. 12 is a top plan view of the surgical instrument caddy shown in FIG. 8 with a tibial broach and a stem component.
Figure 13:
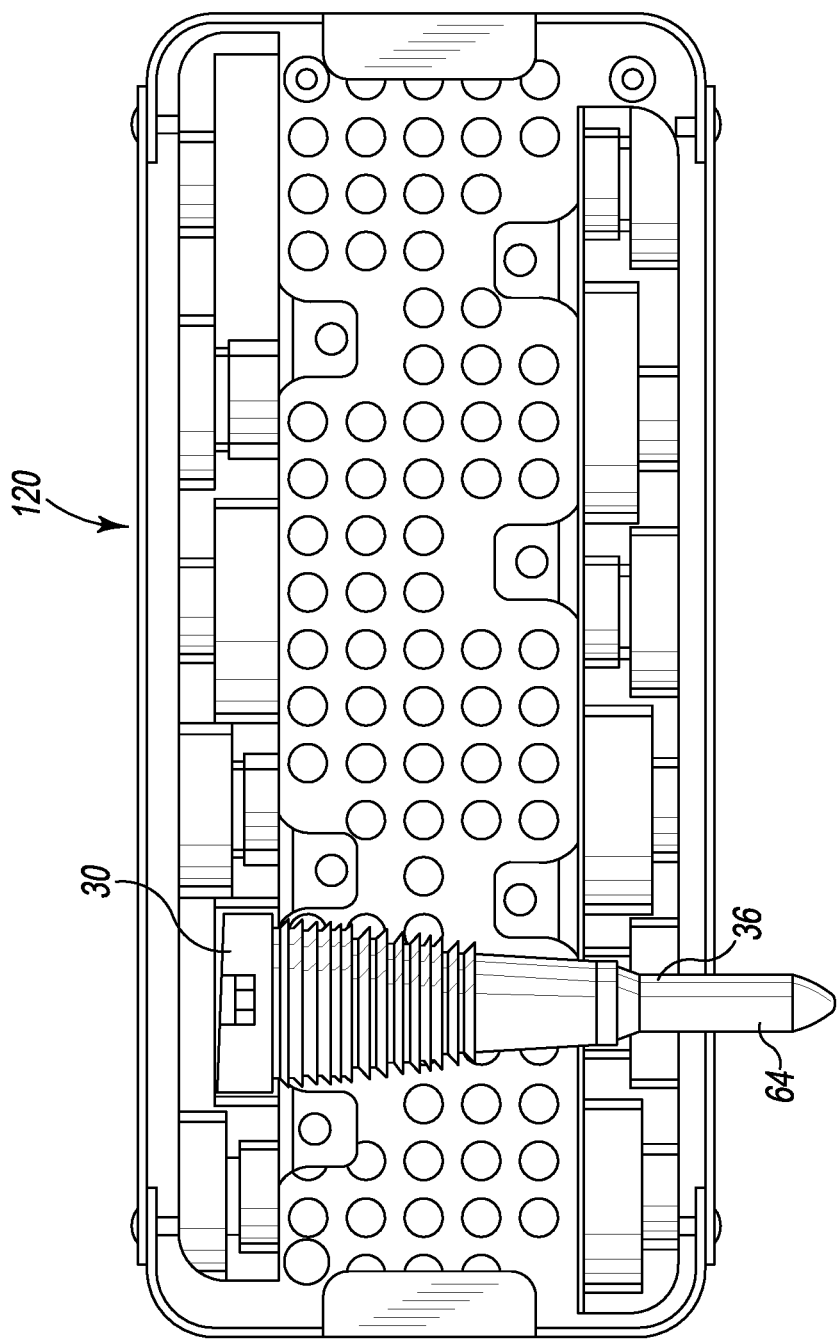
FIG. 13 is a view similar to FIG. 12 showing the stem component assembled to the tibial broach.
Figure 14:
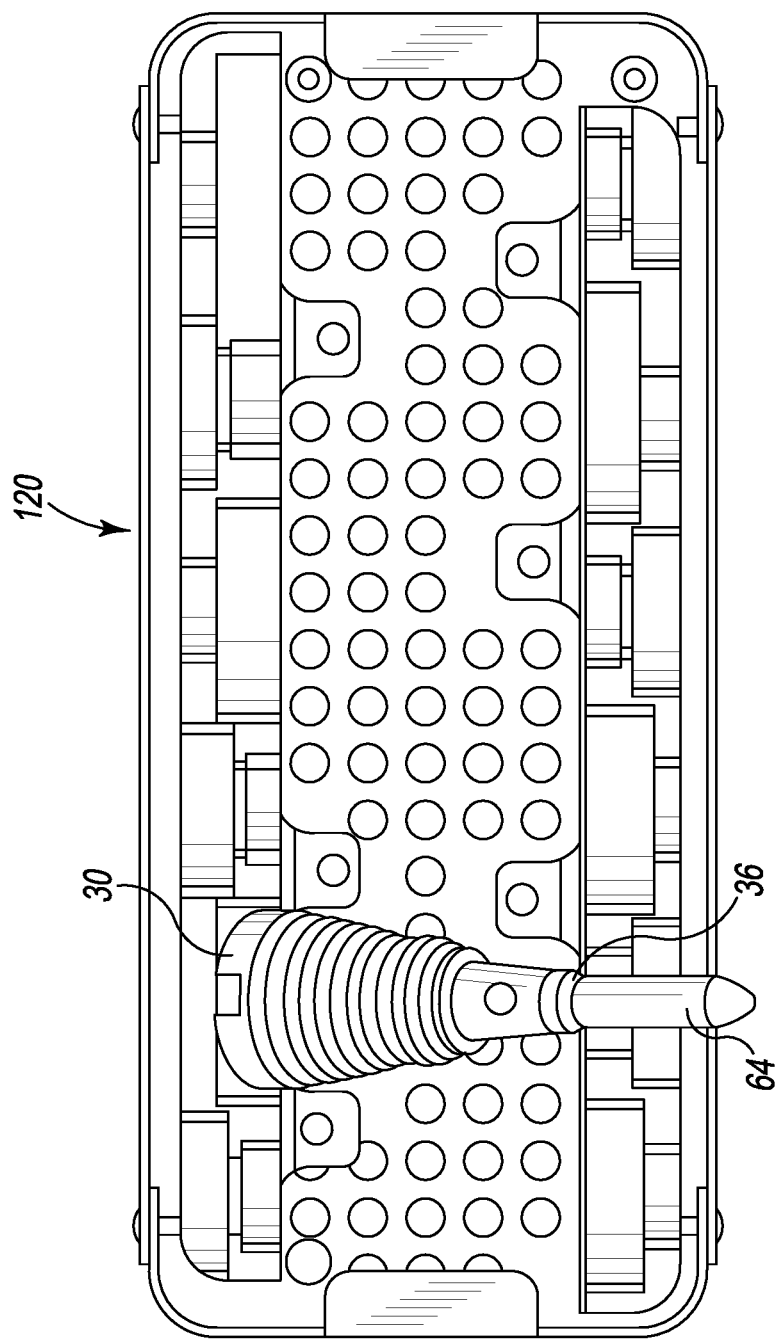
FIG. 14 is a view similar to FIG. 13 showing the stem component assembled to the tibial broach being removed from the surgical instrument caddy.

With the caddy 120 positioned outside of the orthopaedic instrument tray 280, the surgeon selects a tibial broach 30 that is to be inserted into the patient's tibia, i.e. a tibial cutting broach 30 is selected based on a size of the tibial broach 30. The tip 36 of the tibial broach 30 extends outwardly from the slot 176 so that the end 68 of the stem component 64 may be aligned with the tip 36 of the tibial broach 30 from either the longitudinal wall 128 or longitudinal wall 130, as illustrated in FIG. 12. The stem component 64 is then secured to the tibial broach 30 by threading the threads 72 defined on the end 68 of the stem component 64 to the threaded inner wall 62 of the opening 60 of the tibial broach 30, as illustrated in FIG. 13. The side surfaces 151 of the groove 155 engage the oval-shaped outer surface 39 of the base 38 of the tibial broach 30 during advancement of the stem component 64 so that the groove 155 prevents rotation of the tibial broach 30 about its longitudinal axis 37 while the stem component is secured to the tibial broach 30. The surgeon or other user then lifts the stem component 64 to lift the tibial broach 30 from the caddy 120 as illustrated in FIG. 14. By lifting the tibial broach 30 via the stem component 64, the surgeon or other user avoids contacting the cutting teeth 40 formed in the outer surface 34 of the tibial broach 30. If the surgeon chooses to select another sized tibial broach 30, the surgeon or other user may either attach the second stem component 64 of the same size to another tibial broach 30 or position the removed tibial broach 30 back into the caddy 120, unscrew the stem component 64, and attach the stem component 64 to another tibial broach 30. Alternatively, the surgeon or other user may prepare a second tibial broach 30 with a second stem component 64 while a first tibial broach 30 is in use. The second tibial broach 30 is left in the caddy 120 while the first tibial broach 30 is in use. The surgeon or other user may then remove the second tibial broach 30 when needed without having to pause the procedure to secure the second stem component 64.

Figure 16:
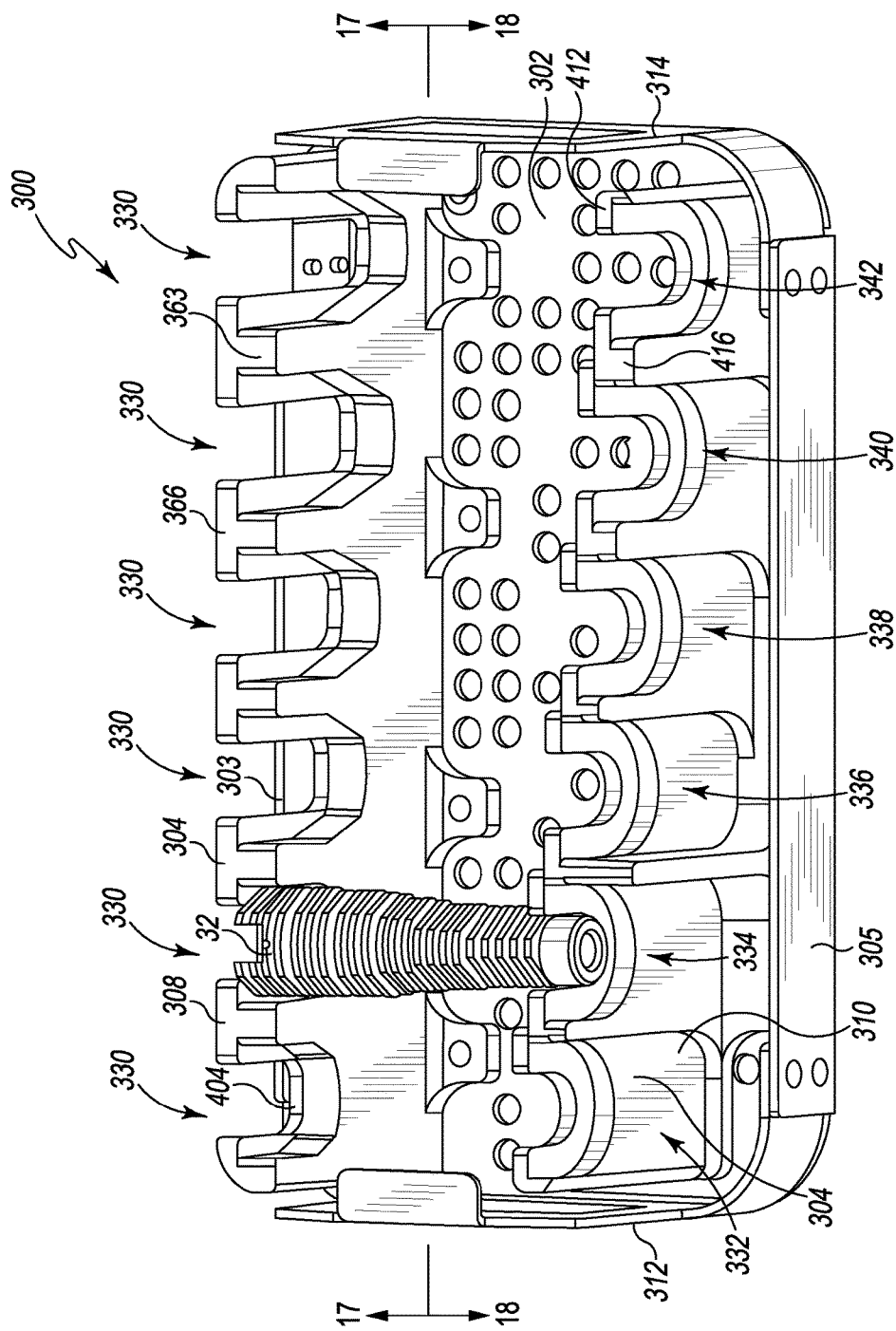
FIG. 16 is a perspective view of another embodiment of a surgical instrument caddy.

Referring now to FIG. 16, another surgical instrument caddy of the system 10 (i.e., the caddy 300) is shown. In the illustrative embodiment, the caddy 300 is configured to receive a plurality of femoral broaches 32 of different sizes, including the femoral broach 32 described above. As shown in FIG. 16, the caddy 300 is configured to house up to six femoral broaches 32, with sizes that range from 30 millimeters to 55 millimeters. It should be appreciated that other size ranges are possible in other embodiments and the caddy may be configured to receive additional or fewer broaches.

Figure 17:
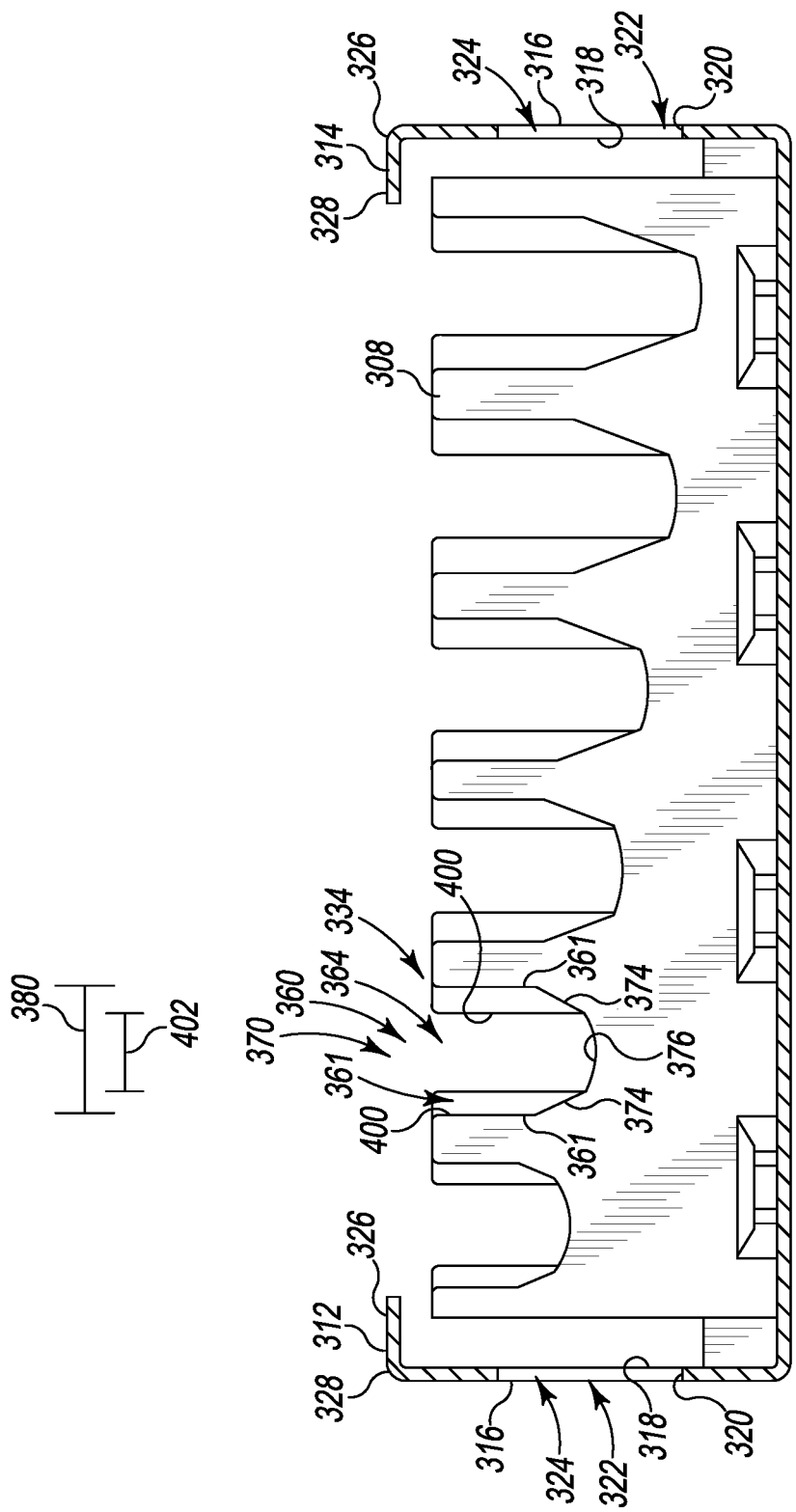
FIG. 17 is a cross-sectional elevation view of the surgical instrument caddy taken along the line 17-17 in FIG. 16.
Figure 18:
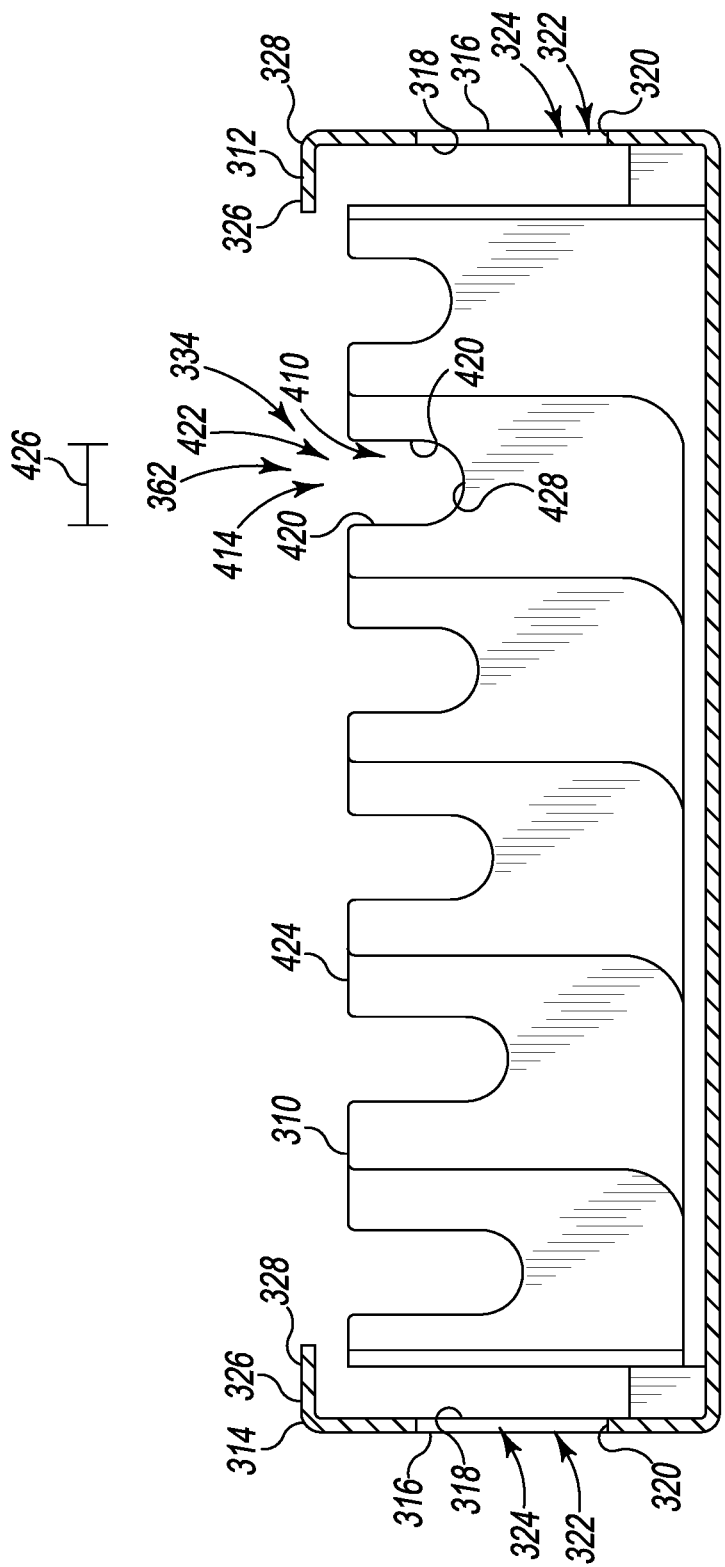
FIG. 18 is a cross-sectional elevation view of the surgical instrument caddy taken along the line 18-18 in FIG. 16.

The caddy 120 includes a bottom wall 302, a pair of outer walls 303, 305, and a pair of end walls 312, 314 positioned at the ends of the outer walls 303, 305. The bottom wall 302, outer walls 303, 305, and end walls 312, 314 are preferably formed from metal. As shown in FIGS. 17-18. Each of the end walls 312, 314 includes an inner opening 316 and an outer opening 318. Side surfaces 320 extend between the inner opening 316 and the outer opening 318 to define a bore 322 through the end walls 312, 314. The bore 322 forms a handle 324 which may be used to lift the caddy 300. Also, a flange 326 extends inwardly from each end wall 312, 314. The flange 326 also forms a handle 328 that may be used to lift the caddy 300.

Referring back to FIG. 16, a plurality of side walls 304 extends upwardly from the bottom wall 302 to define a storage chamber 306. The side walls 304 are positioned between the outer walls 303, 305 and the end walls 312, 314. The side walls 304 are preferably formed from plastic. The side walls 304 include a pair of longitudinal walls 308, 310. As described in greater detail below, the longitudinal walls 308, 310 cooperate to define six broach carriers 330 that are configured to receive the six femoral broaches 32. A broach carrier 332 is positioned adjacent the end wall 312. A second broach carrier 334 is positioned next to the broach carrier 330. Additional broach carriers 336, 338, 340, and 342 are positioned between the broach carrier 334 and the end wall 314 with the broach carrier 342 positioned adjacent the end wall 314. The longitudinal wall 310 has a stepped configuration such that a length of each broach carrier 330 increases in size from the broach carrier 332 to the broach carrier 342. Each broach carrier 330 is configured to hold one of the femoral broaches 32 during sterilization or storage between surgical procedures, as well as assist the surgeon or other user to assemble a broach with a stem component and the instrument handle. In an exemplary embodiment, the broach carrier 332 is configured to retain a 30 millimeter femoral broach 32, the broach carrier 334 is configured to retain a 35 mm femoral broach 32, the broach carrier 336 is configured to retain a 40 mm femoral broach 32, the broach carrier 338 is configured to retain a 45 mm femoral broach 32, the broach carrier 340 is configured to retain a 50 mm femoral broach 32, and the broach carrier 342 is configured to retain a 55 millimeter femoral broach 32. Each broach carrier 334, 336, 338, 340, and 342 is capable of retaining a smaller sized broach.

As shown in FIGS. 17-18, each broach carrier 330 includes a base receptacle 360 configured to receive the base 84 of a femoral broach 32 and a tip mount 362 configured to receive the tip 82 of the femoral broach 32. Each broach carrier 330 has a base receptacle 360 defined in the longitudinal wall 308 and a corresponding tip mount 362 defined in the opposite longitudinal wall 310. In the illustrative embodiment, the configuration of each carrier 330 (and hence each receptacle 360 and tip mount 362) is substantially identical so that only a single carrier 330 will be described in detail below.

Referring to FIG. 17, the base receptacle 360 of the broach carrier 334 includes a groove 361 that is defined in an inner surface 363 (shown in FIG. 16) of the longitudinal wall 308. The groove 361 is sized to receive the base 84 of a femoral broach 32. The base receptacle 360 also includes a channel 364 that is defined in an outer surface 366 (shown in FIG. 16) of the longitudinal wall 308. In the illustrative embodiment, the channel 364 opens into the groove 361. The groove 361 is partially defined by pair of side surfaces 335 that extend inwardly from an opening 370 formed in a top surface 372 of the longitudinal wall 308. An angled surface 374 extends from each side surface 335, and rounded bottom surface 376 extends between the angled surfaces 374 such that the side surfaces 335, the angled surfaces 374, and the bottom surface 376 cooperate to define the groove 361. The side surfaces 335 are spaced a distance 380 that corresponds to the width 99 of the base 84 of the femoral broach 32, and the angled surfaces 374 are shaped to correspond to the angled surfaces 97 of the base 84 of the femoral broach 32 so that the groove 361 prevents rotation of the femoral broach 32 about its longitudinal axis 83.

The channel 364 is partially defined by a pair of side surfaces 400 that extend inwardly from the opening 370. The side surfaces 400 are spaced a distance 402 that is less than the distance 380. The distance 402 is greater than the diameter 103 of the bore 102 of the femoral broach 32 so that the bore 102 is accessible through the channel 364 and the instrument 12 can be attached to the femoral broach 32. Additionally, a size of the femoral broach 32 that may be printed on the femoral broach 32 is viewable through the channel 364. A rounded bottom surface 404 (shown in FIG. 16) extends between the side surfaces 400. The bottom surface 404 is spaced from the bottom surface 404. The bottom surface 404 and the side surfaces 400 cooperate to define the channel 364.

Referring to FIG. 18, the tip mount 362 of the broach carrier 334 includes a slot 410 that is defined in an inner surface 412 (shown in FIG. 16) of the longitudinal wall 310. The slot 410 is sized to receive the tip 82 of a femoral broach 32. The tip mount 362 also includes a channel 414 that is defined in an outer surface 416 (shown in FIG. 16) of the longitudinal wall 310. In the illustrative embodiment, the channel 414 opens into the slot 410. The slot 410 is partially defined by pair of side surfaces 420 that extend inwardly from an opening 422 formed in a top surface 424 of the longitudinal wall 310. The side surfaces 420 are spaced a distance 426. A rounded bottom surface 428 extends between the side surfaces 420 such that the side surfaces 420 and the bottom surface 428 cooperate to define the slot 410. The bottom surface 428 is rounded to correspond to the rounded outer surface 80 of the tip 82 of the femoral broach 32.

Figure 19:
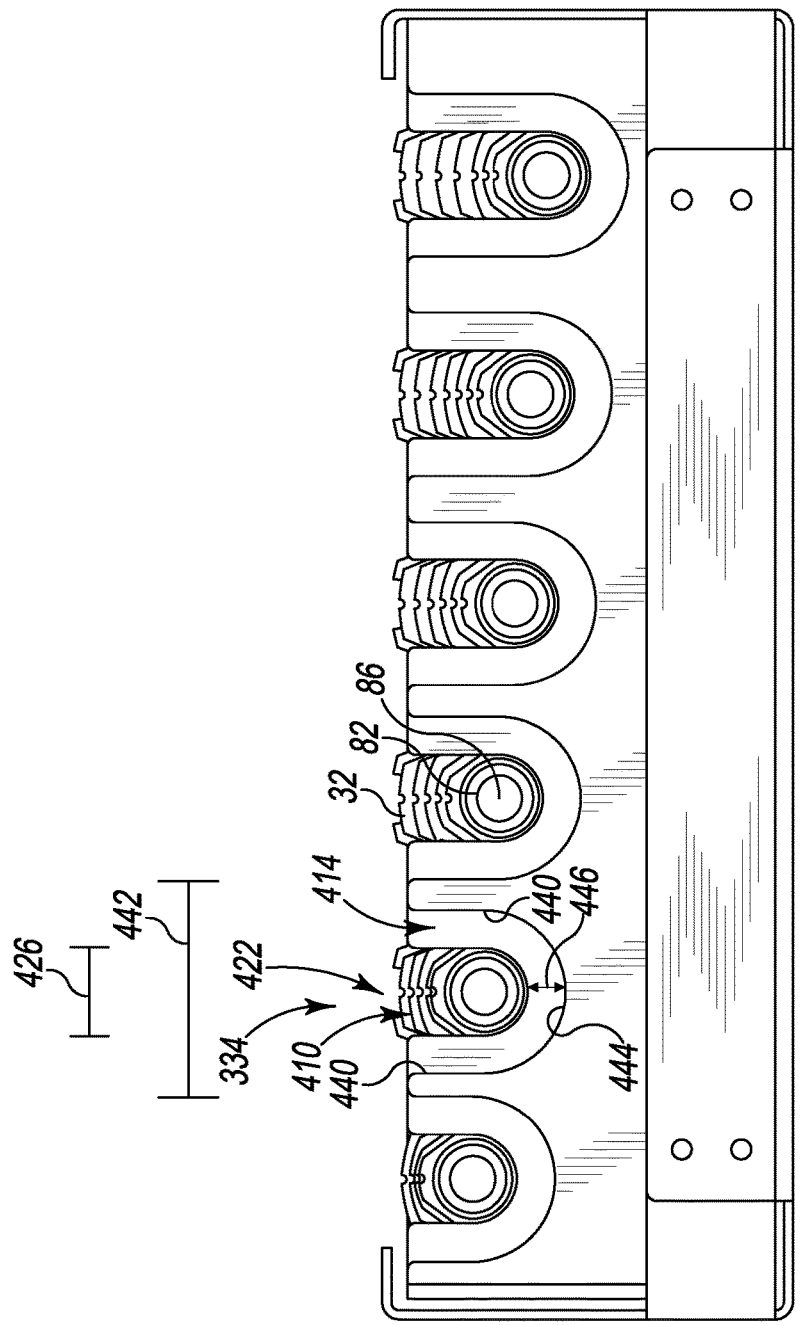
FIG. 19 is a front elevation view of the surgical instrument caddy shown in FIG. 16 with a number of femoral broaches positioned in the surgical instrument caddy.

Referring to FIG. 19, the channel 414 is partially defined by a pair of side surfaces 440 that extend inwardly from the opening 422. The side surfaces 440 are spaced a distance 442 that is greater than the distance 426. The distance 442 is also greater than the diameter 87 of the opening 86 of the femoral broach 32 so that the opening 60 of the femoral broach 32 is accessible through the channel 414. A rounded bottom surface 444 extends between the side surfaces 440. The bottom surface 444 is spaced a distance 446 from the bottom surface 428.

The tips 82 of respective femoral broaches 32 are positioned within respective slots 410 and accessible through the channels 414. The distance 442 between the side surfaces 440 of the channel 414 is greater than the diameter 87 of the opening 86 in the tip 82 of the femoral broach 32. Accordingly, the opening 86 is accessible through the channel 414 such that the stem component 64 can be attached to the femoral broach 32 while the femoral broach 32 is positioned within the caddy 300.

Referring back to FIG. 16, from the end wall 312 to the end wall 314, the base receptacles 360 and tip mounts 362 increase in size. Specifically, the base receptacles 360 and tip mounts 362 of the broach carrier 342 adjacent end wall 314 are deeper than the base receptacle 360 and tip mount 362 of the broach carrier 332 adjacent end wall 312. The groove 361, slot 410, and channels 364 and 414 of the broach carrier 342 are deeper than the groove 361, slot 410, and channels 364 and 414 of the broach carrier 332. Each of the intermittent broach carriers 334, 336, 338, 340 has a depth that is between the depth of the broach carrier 332 and the broach carrier 342.

In use, the caddy 300 is positioned within an orthopaedic instrument tray, similar to the tray 280 shown in FIG. 15. The caddy 300 may be removed from the orthopaedic instrument tray utilizing one of the handles 324, 328 and placed on a surgical table. By removing the caddy 300 from the orthopaedic instrument tray, the femoral broach 32 may be removed from the caddy 300 with the stem component 64, as described below.

Figure 20:
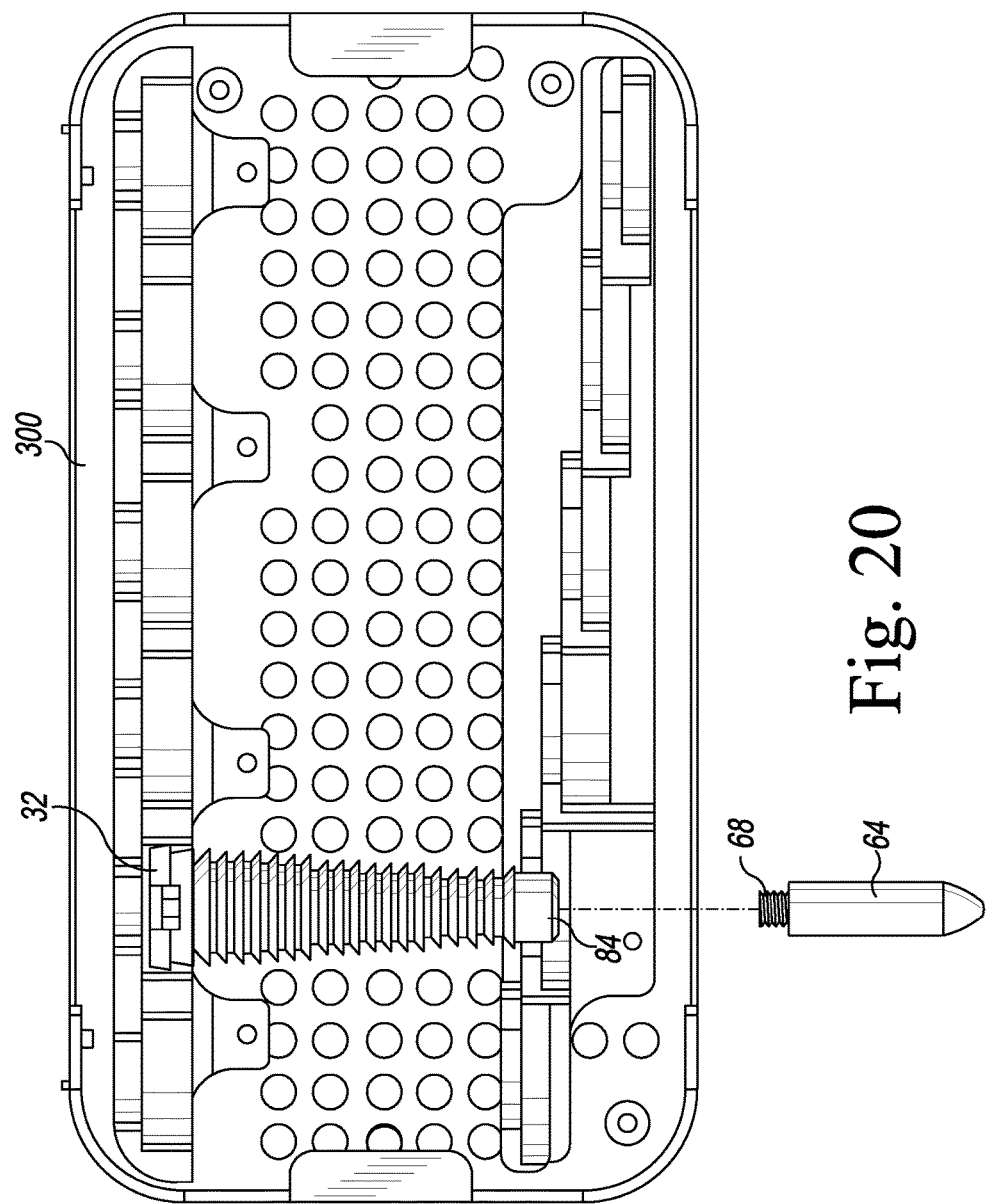
FIG. 20 is a top plan view of the surgical instrument caddy shown in FIG. 16 with a femoral broach and a stem component.
Figure 21:
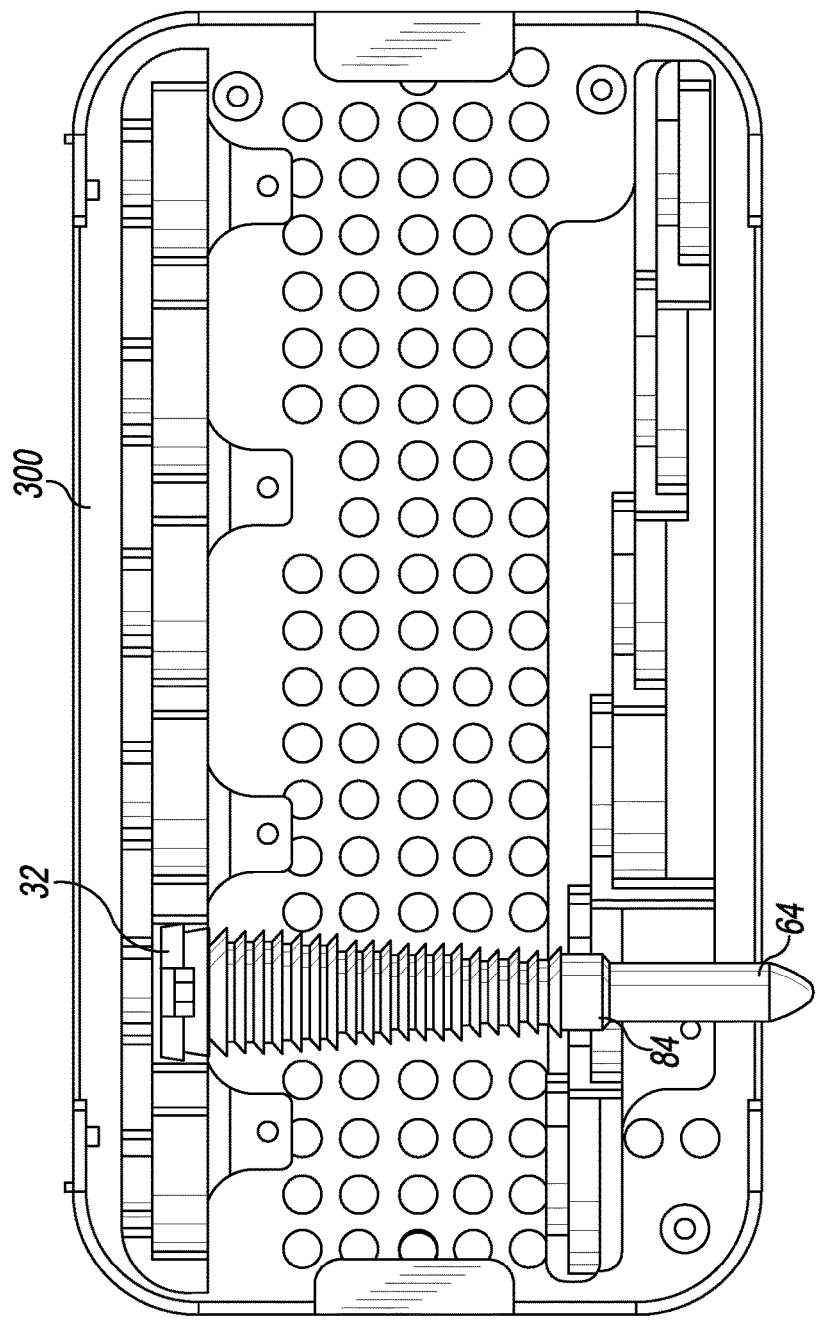
FIG. 21 is a view similar to FIG. 20 showing the stem component assembled to the femoral broach.
Figure 22:
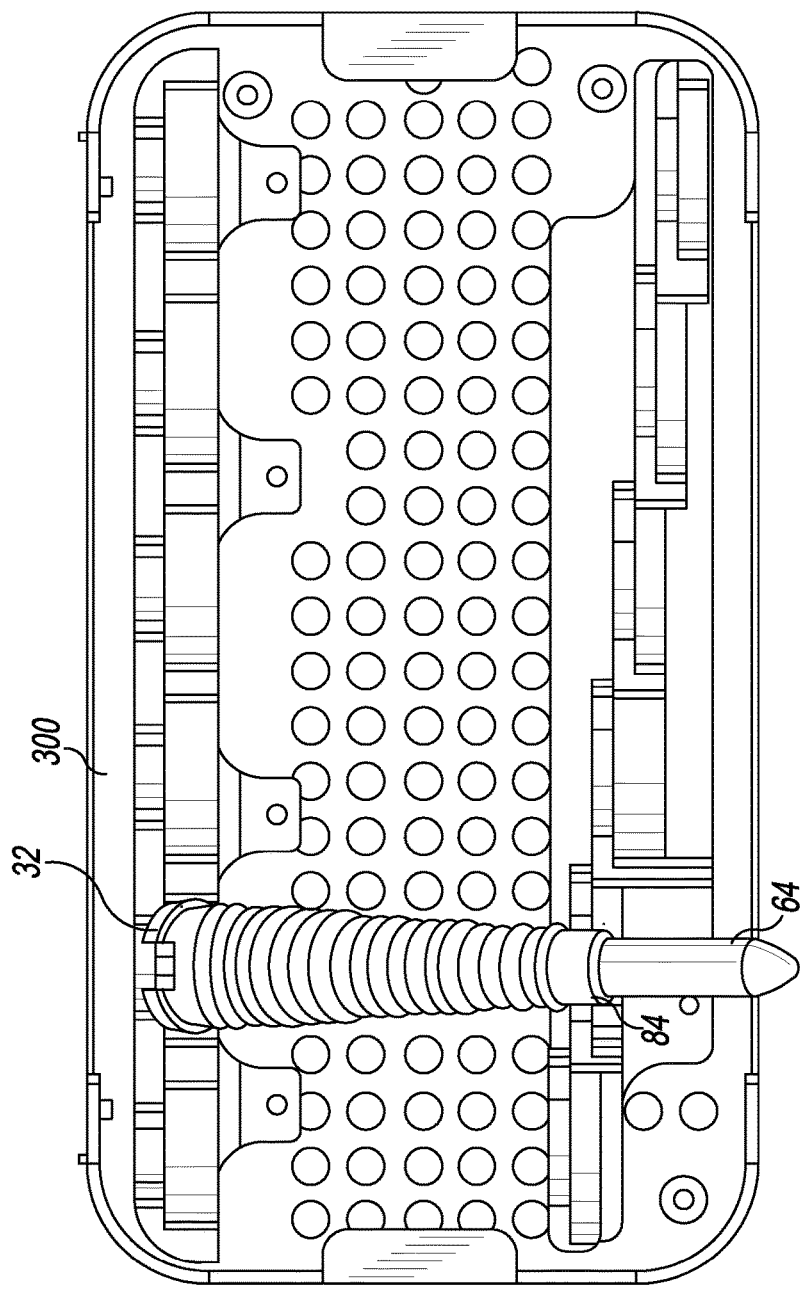
FIG. 22 is a view similar to FIG. 21 showing the stem component assembled to the femoral broach being removed from the surgical instrument caddy.

With the caddy 300 positioned outside of the orthopaedic instrument tray the surgeon or other user selects a femoral broach 32 that is to be inserted into the patient's femur, i.e. a femoral cutting broach 32 is selected based on a size of the femoral broach 32. The tip 82 of the femoral broach 32 extends outwardly from the slot 410 so that the end 68 of the stem component 64 may be aligned with the tip 82 of the femoral broach 32 from the second longitudinal wall 310, as illustrated in FIG. 20. The stem component 64 is aligned with the appropriate femoral broach 32 and secured to the femoral broach 32 by threading the threads 72 defined on the end 68 of the stem component 64 to the threaded inner wall 88 of the opening 86 of the femoral broach 32, as illustrated in FIG. 21. The side surfaces 335 of the groove 361 engage the side surfaces 95 of the femoral broach 32, and the angled surfaces 374 engage the angled surfaces 97 of the femoral broach 32 so that the groove 361 prevents rotation of the femoral broach 32 about its longitudinal axis 83 while the stem component is secured to the femoral broach 32. The surgeon or other user may then lift the stem component 64 to lift the femoral broach 32 from the caddy 300 as illustrated in FIG. 22. By lifting the femoral broach 32 via the stem component 64, the surgeon or other user avoids contacting the cutting teeth 90 formed in the outer surface 80 of the femoral broach 32. If the surgeon or other user chooses to select another sized femoral broach 32, the surgeon or other user may either attach a second stem component 64 of the same size to another tibial broach 30 or may position the removed femoral broach 32 back into the caddy 300, unscrew the stem component 64, and attach the stem component 64 to another femoral broach 32. Alternatively, the surgeon or other user may prepare a second femoral broach 32 with a second stem component 64 while a first femoral broach 32 is in use. The second femoral broach 32 is left in the caddy 120 while the first femoral broach 32 is in use. The surgeon or other user may then remove the second femoral broach 32 when needed without having to pause the procedure to secure the second stem component 64.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic instrument system, comprising:
    a cutting broach including (i) a tapered body extending along a longitudinal axis from a base to a tip and (ii) a plurality of cutting teeth defined in the tapered body, and
    an instrument caddy configured to receive the cutting broach, the caddy comprising a bottom wall, a first side wall extending upwardly from the bottom wall, and a second side wall spaced apart from the first side wall and extending upwardly from the bottom wall to define a storage chamber,
    wherein the first side wall includes an opening and a pair of surfaces extending inwardly from the opening to define a groove sized to receive the base of the cutting broach, and the pair of surfaces are shaped to engage the base of the cutting broach to inhibit rotation of the cutting broach about its longitudinal axis, and
    wherein a slot aligned with the groove extends through the second side wall, the slot being sized to receive the tip of the cutting broach.

2. The orthopaedic instrument system of claim 1, further comprising:
    a stem component including an elongated body and a mounting end sized to be received in an opening defined in an end surface of the tip of the cutting broach to couple the stem component to the cutting broach,
    wherein when the cutting broach is positioned in the caddy, the end surface of the tip of the cutting broach extends outwardly from the slot to permit the stem component to be coupled to the cutting broach.

3. The orthopaedic instrument system of claim 1, further comprising:
a stem component including an elongated body and a mounting end sized to be received in an opening defined in an end surface of the tip of the cutting broach to couple the stem components to the cutting broach,
wherein when the cutting broach is positioned in the caddy, the mounting end of the stem component is received within the slot to permit the stem component to be coupled to the cutting broach.

4. The orthopaedic instrument system of claim 1, wherein:
the cutting broach is a first cutting broach, the opening is a first opening, and the slot is a first slot, and
the caddy further comprises:
(i) a second opening in the second sidewall and a second pair of surfaces extending inwardly from the second opening to define a second groove sized to receive a base of a second cutting broach, and
(ii) a second slot extending through the first sidewall that is sized to receive a tip of the second cutting broach.

5. The orthopaedic instrument system of claim 1, further comprising:
a plurality of cutting broaches,
wherein the first side wall includes a plurality of grooves, each groove being sized to selectively receive a base of one of the plurality of cutting broaches, and
wherein the caddy further comprises a plurality of slots extending through the second side wall, each slot being aligned with one of the plurality of grooves and sized to receive a tip of one of the plurality of cutting broaches.

6. The orthopaedic instrument system of claim 1, further comprising an instrument tray sized and shaped to receive the caddy.

7. The orthopaedic instrument system of claim 1, wherein the caddy further comprises an end wall extending between the first side wall and the second side wall, and a handle formed in the end wall.

8. The orthopaedic instrument system of claim 7, wherein the handle includes an opening extending through the end wall.

9. The orthopaedic instrument system of claim 7, wherein the handle includes a flange extending from the end wall.

10. The orthopaedic instrument system of claim 1, wherein the cutting broach includes one of a femoral cutting broach and a tibial cutting broach.

11. An orthopaedic instrument system, comprising:
an instrument caddy configured to receive a cutting broach, the caddy comprising a bottom wall, a first side wall extending upwardly from the bottom wall, and a second side wall spaced apart from the first side wall and extending upwardly from the bottom wall to define a storage chamber,
wherein the first side wall includes an opening and a pair of surfaces extending inwardly from the opening to define a groove sized to receive a base of the cutting broach,
wherein a slot aligned with the groove extends through the second side wall, the slot being sized to receive a tip of the cutting broach.

12. The orthopaedic instrument system of claim 11, further comprising a cutting broach including (i) a tapered body extending along a longitudinal axis from a base to a tip, (ii) a plurality of cutting teeth defined in the tapered body, and (iii) an opening defined in an end surface of the tip.

13. The orthopaedic instrument system of claim 12, wherein the slot is defined by a pair of side walls that are spaced apart a distance greater than the diameter of the opening defined in the end surface of the tip of the cutting broach.

14. The orthopaedic instrument system of claim 12, further comprising a stem component including an elongated body and a mounting end sized to be received in the opening defined in the end surface of the tip of the cutting broach to couple the stem component to the cutting broach.

15. The orthopaedic instrument system of claim 11, wherein:
the first side wall includes a plurality of grooves, each groove being sized to receive a base of one of a plurality of cutting broaches, and
a plurality of slots extend through the second side wall, each slot being aligned with a groove of the plurality of grooves and being sized to receive a tip of one of the plurality of cutting broaches.

16. The orthopaedic instrument system of claim 11, wherein the caddy further comprises:
an end wall extending between the first side wall and the second side wall, and
a handle formed in the end wall.

17. The orthopaedic instrument system of claim 16, wherein the handle includes an opening extending through the end wall.

18. The orthopaedic instrument system of claim 16, wherein the handle includes a flange extending from the end wall.

19. The orthopaedic instrument system of claim 11, wherein the cutting broach is at least one of a femoral cutting broach or a tibial cutting broach.

* * * * *